United States Patent [19]

Holtkamp

[11] Plant 4,296

[45] Sep. 5, 1978

[54] AFRICAN VIOLET PLANT

[75] Inventor: Reinhold Holtkamp, Isselburg, Fed. Rep. of Germany

[73] Assignee: Gesellschaftsvertrag uber die Erfindergemeinschaft "OPTIMARA", Isselburg, Fed. Rep. of Germany

[21] Appl. No.: 786,854

[22] Filed: Apr. 12, 1977

[51] Int. Cl.[2] ..... A01H 5/00

[52] U.S. Cl. ..... Plt./69

[58] Field of Search ..... Plt./69

*Primary Examiner*—Robert E. Bagwill
*Attorney, Agent, or Firm*—Donald D. Jeffery

[57] ABSTRACT

An African violet having strong stems and 10–12 large pink flowers on each stem. The cultivar is a vigorous grower and is saleable with the first flash of flowers in 7–9 weeks, and full flowering 8–10 weeks.

1 Drawing Figure

The present invention comprises a new and distinct cultivar of African violet plant, botanically known as *Saintpaulia ionantha,* and hereinafter referred to by the cultivar name Indiana. The new cultivar, designated during the breeding and selection process by the designation C 165/9 - 40/77, is a product of a planned breeding program which had the objective of creating a new African violet cultivar with large pink flowers, strong upright stems, short erect peduncles, non-dropping flowers, and the showing of many flowers with the first flash of flowers. These traits in combination were not present in previously available commercial cultivars.

The new cultivar was originated from a cross made in a controlled breeding program in Isselburg, Rhineland, Germany. The female, or seed parent was XIX 4208, a pink unpatented cultivar, color 41-4, having upright and strong flower stems and short peduncles. The male, or pollen parent was BKS VII, an unpatented pink cultivar having large flowers, color 42-4.

The new cultivar Indiana was discovered and selected as a flowering plant within the progeny of the stated cross by me in a controlled environment in Isselburg, Rhineland, Germany. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Indiana which in combination distinguish this African violet as a new and distinct cultivar:

1. Strong upright flower stems.
2. First flash of flowers appears on 6–8 stems, and below the flowers 5–7 more stems with buds are visible.
3. The stems carry up to 12 large flowers on short, strong peduncles.
4. The first stems carry up to 12 flowers each.
5. Vigorous growth, with full flowering appearing in 8–10 weeks.

The accompanying photographic drawing shows a typical specimen plant of the new cultivar. The colors appearing in the photograph are as true as possible with color illustrations of this type.

In the following description, color references are made to The Munsell Limit Color Cascade, 1972 edition, except where general color terms of ordinary significance are obvious.

Botanical classification: *Saintpaulia ionantha,* Ramat. cv. Indiana.

Parentage:

*Male parent.*—BKS VII pink, single, color 42-4.

*Female parent.*—XIX 4208 pink, single, color 41-4.

Propagation: The new cultivar holds its distinguishing characteristics through successive propagations by leaf cuttings and by division of shoots.

Plant: From 9 cm. to 11 cm. tall when grown in pots, and approximately 25 cm. in diameter when fully grown.

*Leaves.*—General form: heart-shaped. Diameter: 60–65 mm. Texture: soft. Aspect: fresh, medium-green, slightly hairy. Veins: well pronounced on underside, reddish. Color (upperside): 21-15. Color (underside): 20-2. Petiole: reddish to brownish.

*Flowers.*—Buds: Ballshaped, 7–8 mm. before opening, color 43-2. Sepals: five, 7 mm. long. Color: 24-15. Calyx: Funnel-shaped. Aspect: Slightly hairy. Peduncle: Slightly hairy, erect, upright.

*Individual flowers.*—Size: Up to 50 mm., almost flat. Color: Upperside: 44-4, with the center of the flower being somewhat darker. Underside: 42-3. Borne: Most of the flower stems carry up to 12 and more flowers. Shape: Five petals, 2 small, 3 large. Corolla: The three larger petals are 25 mm. long and 20–22 mm. wide, the two small petals are 20 mm. long and 15–17 mm. wide. Arrangement: On strong upright peduncles.

*Flowering time.*—In 7–9 weeks after potting, a saleable plant is ready with a nice decorative flowerhead; full flowering in 8–10 weeks.

*Reproductive organs.*—Anthers: Two with four cells, color 26-7 golden yellow; capsule pushes slightly through. Arrangement: Basifixed. Styles: 7–9 mm. long, color 44-3. Pollen color: 27-1. Roots: Well developed when young and active, turning brownish when older.

*Disease resistance.*—Good as experienced to date.

General observations: Indiana is a very vigorous grower with fresh medium green leaves. With the first flash of flowers the plant has 6–8 upright strong stems with up to 12 large pink flowers on short peduncles. Below the flowerhead an additional 5–7 stems with buds appear. When the flower stems carry all open flowers the stems tend to grow sidewards and this provides space for the new flowers. This effects a very long blooming period.

I claim:

1. A new and distinct African violet known by the cultivar name Indiana and particularly characterized as to uniqueness by the combined characteristics of large pink flowers on strong upright stems, the first flash of flowers being on 6–8 stems with 5–7 additional stems therebelow with flowers at the bud stage; up to 12 non-dropping flowers on each stem; medium green leaves, and by its vigorous growth, with full flowering appearing in 8–10 weeks.

* * * * *

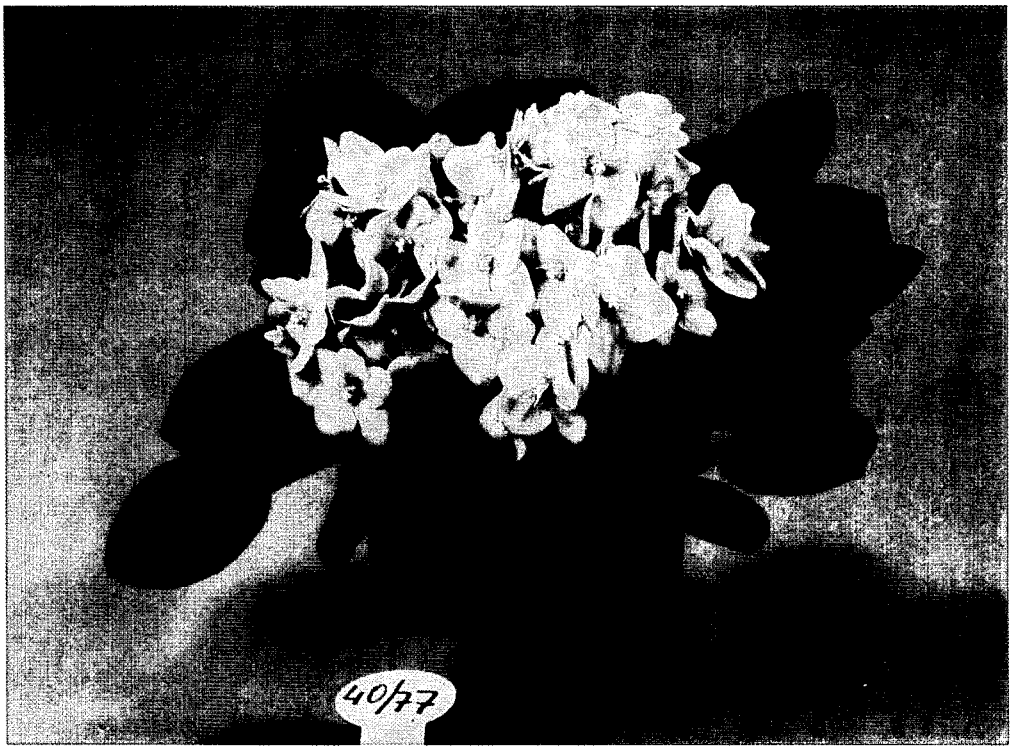
40/77